(12) United States Patent
Stöcker et al.

(10) Patent No.: US 10,955,195 B2
(45) Date of Patent: Mar. 23, 2021

(54) HEAT EXCHANGER FOR AN OXYGENATOR AND METHOD FOR PRODUCING SUCH A HEAT EXCHANGER

(71) Applicant: Raumedic AG, Münchberg (DE)

(72) Inventors: Martin Stöcker, Helmbrechts (DE); Andreas Zeitler, Grafengehaig (DE)

(73) Assignee: Raumedic AG, Münchberg (DE)

( * ) Notice: Subject to any disclaimer, the term of this patent is extended or adjusted under 35 U.S.C. 154(b) by 20 days.

(21) Appl. No.: 15/945,940

(22) Filed: Apr. 5, 2018

(65) Prior Publication Data

US 2018/0224211 A1    Aug. 9, 2018

Related U.S. Application Data

(62) Division of application No. 14/387,129, filed as application No. PCT/EP2013/053853 on Feb. 27, 2013, now abandoned.

(30) Foreign Application Priority Data

Mar. 23, 2012  (DE) .................. 10 2012 204 705

(51) Int. Cl.
*B21D 53/06* (2006.01)
*F28D 7/10* (2006.01)
(Continued)

(52) U.S. Cl.
CPC ............. *F28D 7/103* (2013.01); *B21D 53/06* (2013.01); *F28D 7/16* (2013.01); *F28D 7/1615* (2013.01); *F28D 7/1669* (2013.01); *F28F 9/162* (2013.01); *F28F 21/06* (2013.01); *F28F 21/062* (2013.01); *A61M 1/1698* (2013.01);
(Continued)

(58) Field of Classification Search
CPC .......... F28D 7/103; F28D 7/1669; F28D 7/16; F28D 7/1615; Y10T 29/49361; Y10T 29/4935; Y10T 29/49359
See application file for complete search history.

(56) References Cited

U.S. PATENT DOCUMENTS 3,391,042 A * 7/1968 Schimpf ................. B29C 65/50
156/174
4,003,189 A * 1/1977 Little .................... B65B 27/105
53/590

(Continued)

FOREIGN PATENT DOCUMENTS

DE     1 501 595     12/1969
DE     36 36 583      5/1988
(Continued)

OTHER PUBLICATIONS

English translation JP 02192932A (Year: 1990).*

*Primary Examiner* — Jason L Vaughan
*Assistant Examiner* — Amanda Kreiling
(74) *Attorney, Agent, or Firm* — Boyle Fredrickson S.C.

(57) ABSTRACT

A heat exchanger for an oxygenator comprises multiple tube sections, each having a longitudinal tube axis, wherein the tube sections are disposed as a bundle having a longitudinal bundle axis, and the tube sections are connected to each other in at least one connecting section of the bundle by joining by way of chemical and/or physical bonded joints. A method for producing the heat exchanger is also provided.

13 Claims, 4 Drawing Sheets

(51) Int. Cl.
*F28F 9/16* (2006.01)
*F28F 21/06* (2006.01)
*F28D 7/16* (2006.01)
*A61M 1/16* (2006.01)
*F28D 21/00* (2006.01)

(52) U.S. Cl.
CPC .... *F28D 2021/005* (2013.01); *F28F 2275/12* (2013.01); *Y10T 29/49361* (2015.01)

(56) References Cited

U.S. PATENT DOCUMENTS

| | | | |
|---|---|---|---|
| 4,840,227 A | 6/1989 | Schmidt | |
| 5,465,659 A * | 11/1995 | Minen | B65B 27/10 100/26 |
| 6,508,983 B1 | 1/2003 | McBurney et al. | |
| 6,588,329 B1 * | 7/2003 | Paris | B65B 27/10 100/3 |
| 2001/0016729 A1 * | 8/2001 | Divino, Jr. | A61M 1/1698 604/525 |
| 2004/0052681 A1 | 3/2004 | Mortensen et al. | |
| 2006/0243653 A1 * | 11/2006 | Heinrich | B01D 61/243 210/321.79 |
| 2011/0270147 A1 | 11/2011 | Lauber et al. | |
| 2012/0197363 A1 | 8/2012 | Cloutier et al. | |

FOREIGN PATENT DOCUMENTS

| | | | |
|---|---|---|---|
| DE | 38 05 414 | 9/1989 | |
| DE | 93 13 138.0 | 4/1994 | |
| DE | 196 52 695 | 10/1997 | |
| DE | 10 2010 000 820 | 7/2011 | |
| EP | 1714692 | 10/2006 | |
| JP | 02192932 A * | 7/1990 | F28F 21/062 |

* cited by examiner

HEAT EXCHANGER FOR AN OXYGENATOR AND METHOD FOR PRODUCING SUCH A HEAT EXCHANGER

CROSS-REFERENCE

This application is a divisional of U.S. Non-Provisional patent application Ser. No. 14/387,129, filed Sep. 22, 2014, which is a U.S. national stage application of PCT Application Serial No. PCT/EP2013/053853, filed Feb. 27, 2013, which claims priority to German patent application DE 10 2012 204 705.0, filed Mar. 23, 2012, the entirety of each of which is hereby expressly incorporated herein by reference.

FIELD OF THE INVENTION

The invention relates to a heat exchanger for an oxygenator and to a method for producing such a heat exchanger.

BACKGROUND OF THE INVENTION

An oxygenator is an integral part of an extracorporeal blood circuit during open heart surgery. Temperature control takes place in a heat exchanger of the oxygenator by exchanging heat between the blood and a heat exchanger medium.

A heat exchanger is known from DE 10 2010 000 820 A1, which comprises multiple tube sections that are knitted to each other by transversely extending knitted seams, known as support threads, to form a mat. The mat is rolled to form a heat exchanger body, and a heat exchanger is produced therefrom. Additional heat exchangers comprising knitted tube mats are known from DE 28 25 065 A1 and from WO 2011/139392 A1.

It is disadvantageous that a heat exchanger, in particular tube sections used therefor, can become polluted and/or damaged during production.

SUMMARY OF THE INVENTION

It is an object of the present invention to improve a heat exchanger, in particular in such a way that the heat exchanger can be produced in an uncomplicated manner, and thus in particular the risk of pollution and/or damage during production is reduced.

According to an aspect of the invention, it was recognized that the risk of pollution and/or damage during the production of a heat exchanger is reduced when tube sections are connected to each other by joining by way of chemical and/or physical bonded joints. It is thus not necessarily required to connect the tube sections to each other using a knitting method. In particular, it can thus be excluded that the tube sections are constricted by the knitted seams, and thus a flow surface in the tube interior, this being the tube cross-sectional surface, is reduced. Depending on the operating principle, the heat exchanger can be used in such a way that blood flows in the interior of the tube sections and heat exchanger medium flows in intermediate spaces formed between the tube sections, or conversely, that heat exchanger medium flows in the interior of the tube sections and blood flows in the intermediate spaces. The individual flow cross-sections of the tube sections are not impaired by the joining according to the invention by way of chemical and/or physical bonded joints. The individual tube sections are also securely fixed and connected to each other to form a bundle. This means that an independent bundle that is dimensionally stable in itself is formed by the adhesive bonding according to the invention of the individual tube sections to each other. The bundle is substantially cylindrical. Handling, and in particular a subsequent joining process of the bundle in a housing of a heat exchanger, is simplified. The bundle as a whole, and not the individual tube sections, can be connected, and more particularly adhesively bonded, to the housing. Such a production method is particularly robust and not susceptible to failure. Moreover, the heat exchanger has reduced pollution. In particular, it can be precluded that abrasion of a support thread, which would occur as a result of knitting the tube sections together to form a mat, causes dust accumulation on the heat exchanger. The heat exchanger can be produced in a less complicated manner, and in particular more reliably. The heat exchanger is particularly economical to produce, since the reject rate, which is to say the number of heat exchangers that are produced but are unusable, is reduced. Moreover, the heat exchanger enables improved use, since a more uniform flow of the blood between the tube sections is assured. In particular, flow of the blood between the tube sections is not impaired by support threads. As a result, turbulences of the blood can be prevented. Since no obstacles to the flow are present along the flow path of the blood in the heat exchanger, the blood can be pumped at an essentially constant pressure through the heat exchanger. In particular, it is not required to overcome increased pumping pressure so as to overcome constrictions and/or obstacles in the heat exchanger. It is thus ensured that reduced damage to the blood occurs with use of the heat exchanger. The heat exchanger comprises multiple tube sections, each having a longitudinal tube axis. The tube sections are disposed in the bundle having a longitudinal bundle axis. The bundle comprises at least one connecting section, in which the tube sections are connected to each other by joining. The tube sections are connected to each other by adhesive bonding. The connection by adhesive bonding can be produced quickly and in an uncomplicated manner and allows high and consistently reliable bonded joints of the tube sections with each other. The tube sections are exclusively connected to each other by adhesive bonding. The construction of the heat exchanger is robust. In particular further processing of an adhesively bonded bundle and handling are simplified. The bundle has a cross-sectional surface that is oriented perpendicularly to the longitudinal bundle axis, in particular a circular cross-sectional surface. It is also possible, depending on use, to dispose the tube sections in a bundle shape that differs from this, which is to say having a cross-sectional surface that differs from a circular shape and that is disposed perpendicularly to the longitudinal bundle axis. By being able to dispense with knitted threads when fixing the tube sections to form a bundle, the individual tube sections can follow the flow movement, for example in a freely swinging or oscillating fashion. The flow of the blood, or of the heat exchanger medium, is thus not impaired. In addition, flow quality is improved, resulting in improved mixing of the media. As a result, the efficiency of the heat exchanger is increased.

The heat exchanger according to the invention has increased stability and rigidity. It is additionally stabilized, and in particular rigid, by the at least one connecting section comprising an adhesive. In particular a casting resin, and more particularly acrylate, phenolic resin, silicone, polyurethane or copolymer, can be used as the adhesive. It is also possible to use a thermoplastic casting compound as the adhesive. An acrylate can be cured by way of UV radiation, for example. However, it is also possible to achieve crosslinking using addition-crosslinking or radically crosslinking casting resins. A polycondensation reaction for cross-linking, or catalytic cross-linking, such as platinum-catalyzed silicone, is also possible. No cross-linking occurs with thermoplastic casting compounds, such as polyurethane.

A heat exchanger according to an aspect of the invention exhibits improved blood compatibility. Moreover, the tube sections made of plastic material, which can be made in particular of polyurethane, have a low mass. An individual tube section typically weighs approximately 0.035 g. The tube sections to be connected, which is to say the bundle without the connecting sections, weighs no more than 200 g, wherein the mass can deviate depending on the size of the bundle, which is to say as a function of the number and/or length of tube sections. The tube sections have high mechanical flexibility and enable an increased design variety in the production of the heat exchanger, and in particular in the configuration of the bundle.

A heat exchanger according to an aspect of the invention exhibits improved efficiency. By disposing the tube sections in such a way that the longitudinal tube axes thereof form an angle with the longitudinal bundle axis which is greater than 10°, more particularly greater than 20°, and more particularly greater than 30°, the flow of blood or of the heat exchanger medium, in particular water, on the outer sides of the tube sections is improved. The blood, or the heat exchanger medium, flows better around the tube sections through which the respective other medium flows, whereby the contact surface, which is to say the heat exchanger surface, is increased. The heat exchange between the blood and the heat exchanger medium is improved. In particular, the tube sections are disposed in such a way that the longitudinal tube axes are oriented parallel to each other.

In a heat exchanger according to another aspect of the invention, the efficiency of the heat exchanger is additionally increased. By disposing the tube sections with the longitudinal tube axes at least sectionally in a non-linear fashion, and more particularly in a curved fashion, the flow around the tube sections is improved. The tube sections in particular have a bending radius. In particular, it is conceivable that the tube sections are designed to be undulated or sinusoidal along the bundle, having a peak and a valley.

A heat exchanger according to yet another aspect of the invention is robust. The bundle is protected inside the housing. The housing is made in particular of plastic material, and more particularly of transparent plastic material.

A heat exchanger according to still another aspect of the invention exhibits increased stability By providing each bundle end with a connecting section at which the tube sections are connected to each other, the bundle has inherent stability. In particular, it is thus possible to preserve an arrangement of the tube sections into a bundle having a desired orientation of the longitudinal tube axes.

A heat exchanger according to still another aspect of the invention is particularly robust and stable. By connecting the bundle to the housing, reliable, and in particular trouble-free, use of the heat exchanger in the oxygenator is assured. By connecting the bundle to the housing, in particular on the connecting section, it is precluded that the tube sections are impaired, in particular polluted and/or damaged, when the bundle is connected to the housing.

A heat exchanger according to yet another aspect of the invention enables improved flow properties for the blood and/or the heat exchanger medium. As a result, the efficiency of the heat exchanger is improved. The bundle has a round cross-sectional surface. It is also conceivable that the bundle has an oval, rectangular, square or another polygonal cross-sectional surface, for example.

A heat exchanger according to still another aspect of the invention has increased tube section density, which is to say the number of tube sections in the bundle is increased. Since knitted threads are not required, the individual tube sections can be disposed more closely together, which is to say a perpendicular distance between outside walls of two neighboring tube sections can be reduced. The perpendicular distance is no more than 200 µm, and more particularly no more than 100 µm. A tube wall thickness is approximately 0.01 mm to 0.2 mm. An inside diameter of the tube section is approximately 0.1 mm to 2.0 mm. An outside diameter of the tube section, which results from the sum of the inside diameters and twice the wall thickness, is accordingly approximately 0.12 mm to 2.4 mm. By being able to dispose a comparably larger number of tube sections in a bundle, the heat exchanger surface can be increased at the same bundle size, which is to say at the same cross-sectional surface of the bundle. As an alternative, the length of the heat exchanger along the longitudinal bundle axis can be reduced for a specified heat exchanger performance, wherein the overall heat exchanger surface remains constant. Due to the reduced heat exchanger length, the flow resistance through the heat exchanger can be reduced, whereby an improvement in blood compatibility is achieved.

It is another object of the present invention to improve a method for producing a heat exchanger for an oxygenator in such a way that in particular the production thereof is possible in a more reliable and less complicated manner, and that the heat exchanger thus produced in particular has improved usage properties.

This object is achieved according to the invention by a method having the features described in claim 1. That method includes providing multiple tube sections, each having a longitudinal tube axis; disposing the tube sections to form a bundle having a longitudinal bundle axis in which the longitudinal tube axes are in particular oriented parallel to each other; and connecting the tube sections to each other on at least one connecting section of the bundle by joining the tube sections by way of chemical and/or physical bonded joints According to the invention, it was recognized that tube sections to be disposed in a bundle are to be connected to each other by a joining method by way of chemical and/or physical bonded joints. It is therefore possible that mechanical connecting, such as knitting the tube sections together to form a mat and subsequent rolling of the mat onto a core to form a bundle, is not required. In particular, it is therefore possible to avoid the additional method steps, such as knitting the tube sections together to form a mat and winding the mat to form a bundle. The method is uncomplicated and quick to carry out. Moreover, the risk of possible damage to the tube sections as a result of constriction by the knitted threads and/or by pre-stressing, which in particular can result in tearing, of the tube sections can be avoided. Pollution of the tube sections, and more particularly dust accumulation, when the tube sections are knitted together, by abrasion of the knitted thread, are likewise precluded. A heat exchanger produced by way of this method has additional advantages, which were already described above based on the heat exchanger and to which is hereby made reference. In the method, multiple tube sections are provided, which are made available, for example, cut to a particular length. The tube sections are disposed in a bundle, wherein the longitudinal tube axes of the tube sections are in particular oriented parallel to each other. It is conceivable for the tube sections to be disposed in a sleeve-shaped mounting to form the bundle. It is also possible for the tube sections to be actively held by a gripping tool, in particular by gripping pliers, wherein the gripping pliers have a shape that corresponds to the bundle.

A method according to claim 2 allows the tube sections to be disposed in a desired arrangement in a rapid and uncomplicated manner. It is thus possible to dispose the individual tube sections at an angle different from 0° relative to the longitudinal bundle axis, the angle in particular being greater than 10°, in particular greater than 20°, and in particular greater than 30°. As an alternative or in addition, the tube sections can be disposed in a curved manner along the longitudinal bundle axis. In particular, it is advantageous if the two, mutually opposing bundle ends are initially connected to each other, in particular by adhesive bonding, and subsequently the one bundle end is twisted about the longitudinal bundle axis and/or the bundle is compressed along the longitudinal bundle axis.

In a method according to claim 3, a prefabricated bundle is inserted into a housing, in particular a tubular housing. At the bundle ends, for example, a prefabricated bundle comprises mutually connected, in particular adhesively bonded, tube sections, which after connection were twisted about the longitudinal bundle axis and/or were compressed along the longitudinal bundle axis. In particular an outer shape of the bundle, such as a cylindrical shape, is adapted to an inner contour of the housing.

In a method according to claim 4, the bundle is inserted into the housing in such a way that in each case a connecting section disposed on a bundle end is disposed at least sectionally outside the housing. Handling of the bundle during insertion into the housing is thus simplified. In particular, it is possible to sever the regions of the connecting sections which protrude over the housing and thus create in particular a flush termination of the bundle on the housing.

A method according to claim 5 simplifies the production of multiple bundles. Such a method is especially suited in particular for mass production, since it is possible to produce multiple bundles simultaneously. For example, it is conceivable that tube sections having large lengths, which in particular correspond to multiple times a desired length of a heat exchanger, are disposed in bundle form, wherein the tube sections are connected to each other at a heat exchanger length. In particular, it is thus conceivable that tube sections are connected to each other at regular intervals in a connecting section, and subsequently such a "continuous" bundle is cut at the connecting sections, so that multiple bundles are available, having a connecting section disposed at the bundle ends in each case.

BRIEF DESCRIPTION OF THE DRAWINGS

Exemplary embodiments of the invention are described in more detail hereafter based on the drawing. In the drawings.

DETAILED DESCRIPTION OF AT LEAST ONE PREFERRED EMBODIMENT

Figure 1:
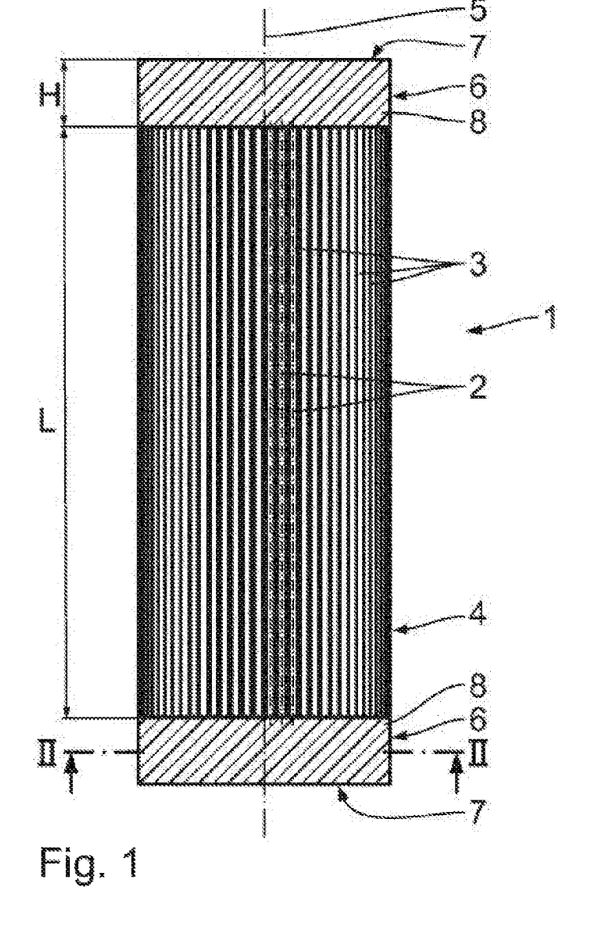
FIG. 1 is a side view of an inventive heat exchanger according to a first embodiment.
Figure 2:
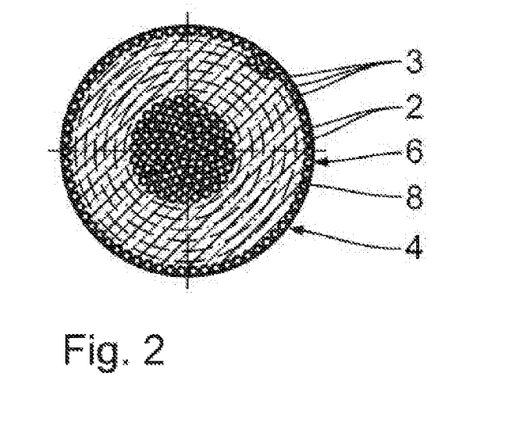
FIG. 2 is a sectional illustration according to line II-II from FIG. 1.
Figure 3:
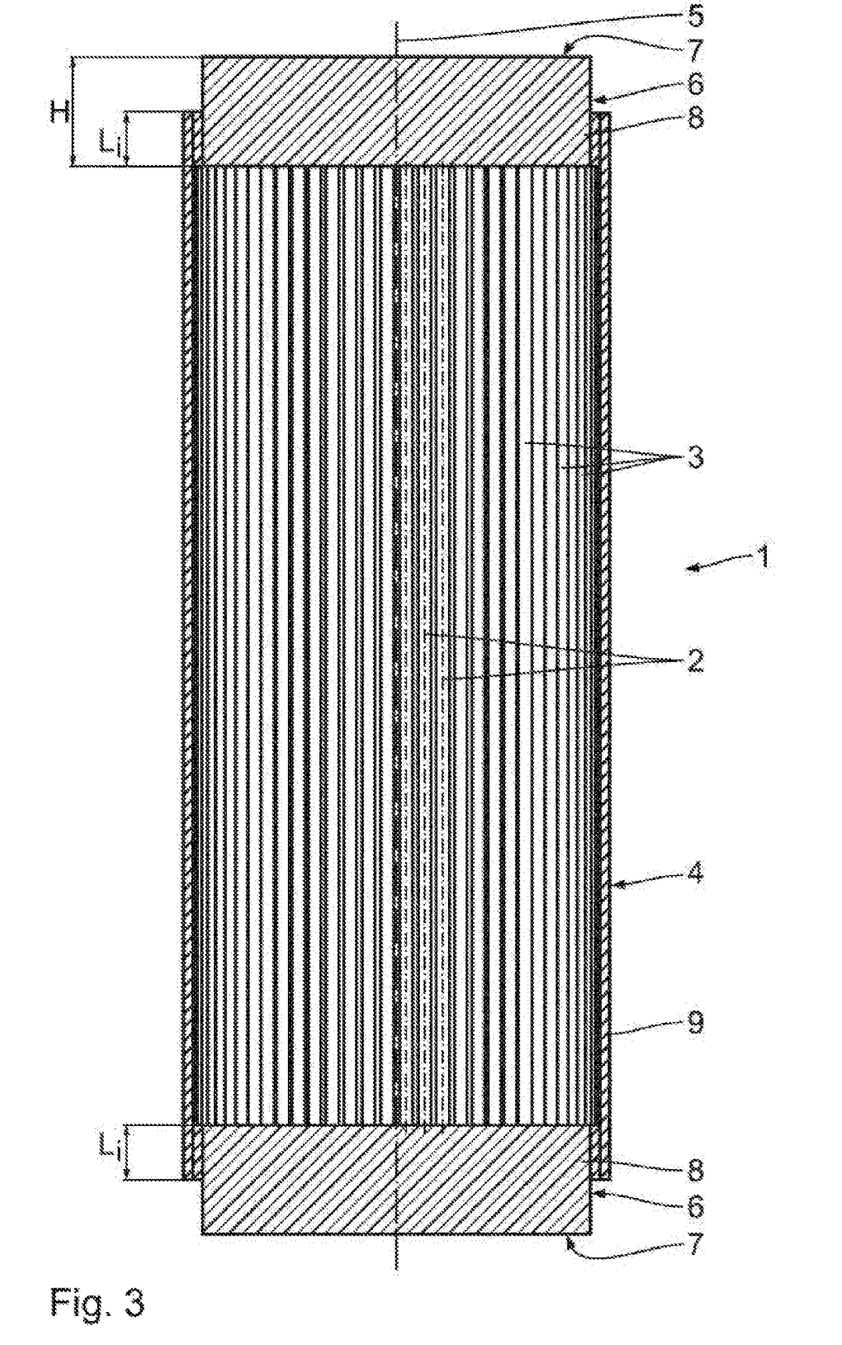
FIG. 3 is a view of a bundle in a housing corresponding to FIG. 1.

A heat exchanger 1 shown in FIGS. 1 to 3 comprises multiple tube sections 3, each having a longitudinal tube axis 2. The tube sections 3 are made of plastic material, and more particularly of polyurethane (PUR). Other plastic materials can also be used to produce the tube sections 3, such as polyester, in particular polyethylene terephthalate (PET) or polybutylene terephthalate (PBT), polyamides and co-polymers or polyurethanes and copolymers, in particular polyether polyurethane or polyester polyurethane.

According to the shown exemplary embodiment, the tube sections 3 are disposed to form a bundle 4, which has a longitudinal bundle axis 5. The tube sections 3 are disposed in each case in such a way that the longitudinal tube axes 2 thereof are in each case oriented parallel to each other and parallel to the longitudinal bundle axis 5.

The tube sections 3 are connected to each other in two two connecting sections 6, which are in each case disposed on bundle ends 7, by adhesive bonding, which is to say by joining by way of chemical and/or physical bonded joints. According to the shown embodiment, the tube sections 3 are exclusively connected by an adhesive 8 in the respective connecting section 6. This means that the individual tube sections 3 are directly connected to each other.

The bundle 4 has a substantially cylindrical basic shape. A cross-sectional surface oriented perpendicularly to the longitudinal bundle axis 5 is circular. However, it is essentially also conceivable to use other basic shapes for the bundle 4. The connecting sections 6 likewise have a cylindrical shape and have a height H that is oriented along the longitudinal bundle axis 5. According to the shown exemplary embodiment, the height H is 5 mm.

Figure 5:
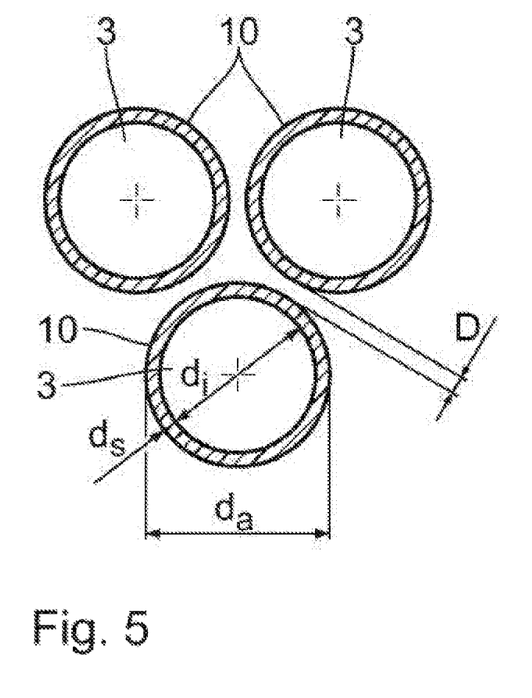
FIG. 5 is an enlarged detailed illustration of tube sections of the bundle corresponding to FIG. 2.

The heat exchanger 1 has a length L, which is delimited by the two connecting sections 6 disposed opposite each other at the bundle ends 7. Within the length L, the heat exchange takes place between the heat exchanger medium, and more particularly water, and the blood flowing between the tube sections, and more particularly in a manner that is directed counter to the flow direction of the heat exchanger medium. According to the shown exemplary embodiment, the length L is approximately 170 mm. The length L of the heat exchanger 1, the number of tube sections 3 disposed to form the bundle 4, the respective inside tube diameter of the tube sections 3, and the respective wall thickness of the tube sections 3 are selected in accordance with the requirements in regard to the heat exchanger 1. According to the detailed illustration of the exemplary embodiment of FIG. 5, an inside diameter $d_i$=0.67 mm, an outside diameter $d_a$=0.79 mm, and a tube wall thickness $d_s$=0.06 mm. In particular the number of tube sections 3 that are used can vary as a function of the patient's size, which is to say the volume of the blood to be circulated.

The bundle 4 has a constant cross-sectional surface along the longitudinal bundle axis 5. In particular, the respective cross-sectional surfaces at the two bundle ends 7 are identical in size. A perpendicular distance D between outer walls 10 of two neighboring tube sections 3 is no more than 200 µm. The distance D is in particular no more than 100 µm. It is thus assured that the tube sections 3 are combined with greater density to form the bundle 4.

As is shown in FIG. 3, the bundle 4 is disposed at least sectionally in a housing 9. The connecting sections 6 each protrude half way, which is to say with approximately 50% of the height H, from the housing 9. This means that an inner section having a length $L_i$ of the connecting section 6 is disposed inside the housing 9. On the inner region of the connecting sections 6, which in particular has a cylindrical design, these are adhesively bonded via the outer lateral cylinder surface thereof to an inner side of the housing 9. For this purpose, in particular the same adhesive 8 is used as for connecting the individual tube sections 3. The length $L_i$ is approximately 50% of the height H of the connecting section 6, which is to say approximately 2.5 mm, and thereby assures secure connection of the bundle 4 in the housing 9.

Figure 4:
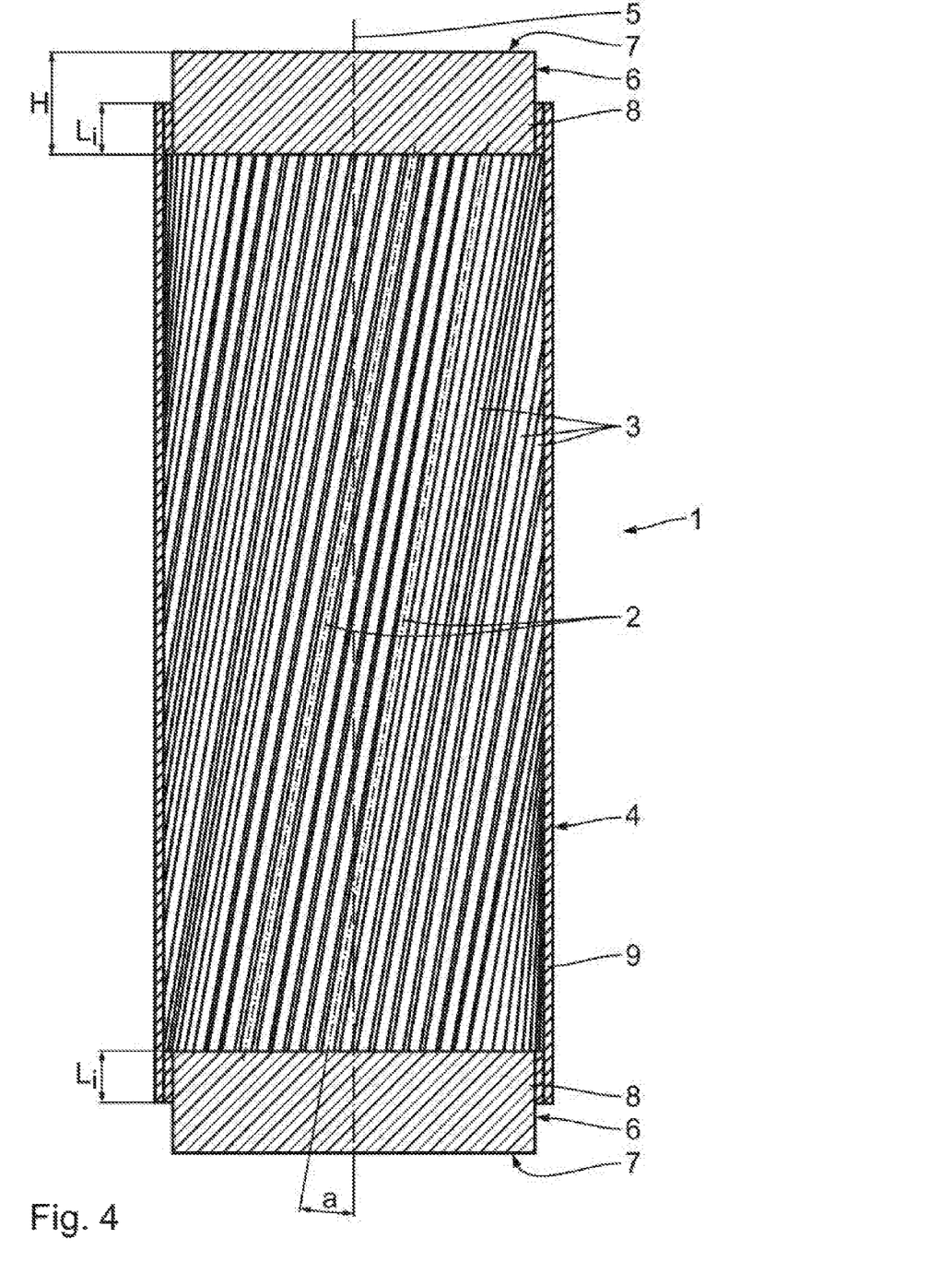
FIG. 4 is a view of a heat exchanger according to a further embodiment corresponding to FIG. 1.

Based on the illustration of FIG. 4, a further embodiment of a heat exchanger will be described hereafter. Identical parts, which were already described based on FIGS. 1 to 3, are denoted by identical reference numerals and will not be described again in detail.

The essential difference of the heat exchanger 1 according to the further embodiment is that the tube sections 3 are disposed in such a way that the longitudinal tube axes 2 form an angle a with the longitudinal bundle axis 5 which in particular is greater than 10°, in particular greater than 20°, and in particular greater than 30°. It is thus assured that the flow behavior of the blood through the heat exchanger 1 is improved. In addition or as an alternative, it is possible for the tube sections 3 to be disposed in the bundle 4 in such a way that the longitudinal tube axes 2 are at least sectionally disposed in a non-linear fashion, and more particularly in a curved fashion relative to the longitudinal bundle axis 5.

A method for producing a heat exchanger 1 according to the invention will be described in more detail hereafter. First, multiple tube sections 3 having preferably identical lengths are provided. Depending on the required heat exchanger capacity, the number and length of the tube sections 3 can vary. The tube sections 3 are disposed in a sleeve-shaped mounting, in particular a cylindrical pipe, to form a bundle 4, wherein the longitudinal tube axes 2 of the tube sections 3 are preferably oriented parallel to the longitudinal bundle axis 5. Thereafter, the tube sections 3 are connected in the at least one connecting section 6, and more particularly in two connecting sections 6 that are disposed in each case at one bundle end 7 of the bundle 4. The tube sections 3 are connected to each other by adhesive bonding, in particular by way of acrylic resin. By adhesively bonding the tube sections 3 to each other, the tube ends are hermetically sealed and thus protected from internal contamination. Thereafter, the adhesively bonded bundle 4 is inserted into the housing 9, wherein each of the two connecting sections 6 protrudes at the end face from the tubular housing 9. So as to assure compression and/or curvature of the tube sections 3 of the bundle 4, initially a first connecting section 6 is adhesively bonded to the section of the connecting section 6 remaining in the housing 9 on an outer lateral cylinder surface in the housing 9. As a result, the bundle 4 is closed off and sealed in the housing 9. The adhesive surface is large and assures secure attachment of the first connecting section 6 in the housing. The bundle 4 can now be twisted about the longitudinal bundle axis 5, so that the longitudinal tube axes 3 of the tube sections 3 are disposed at an angle a relative to the longitudinal bundle axis 5. In addition or as an alternative, it is possible to compress the bundle 4 along the longitudinal bundle axis 5, so that the tube sections 3 at least sectionally have a curvature. For this purpose, the second, free connecting section 6 is compressed and/or twisted in relation to the first connecting section that is fixed in the housing 9. The free connecting section 6 is held on the outer section protruding from the housing by way of a gripping tool. As soon as the second connecting section 6 has been brought into a desired position, it can likewise be adhesively bonded along an outer lateral cylinder surface to an inner side of the housing 9. As an alternative, however, it is also possible to achieve positioning of the connecting sections 6 with respect to each other by positioning the two connecting sections 6 relative to each other so as to be freely movable in relation to the housing 9 by way of a respective gripping tool, and by subsequently adhesively bonding them in the housing 9. After the bundle 4 has been adhesively bonded to the housing 9, the portions of the connecting sections 6 protruding over the housing 9 are severed. This re-opens the ends of the tube sections 3.

It is also conceivable for the bundle 4 to be held in the housing by a press fit in the region of the connecting sections 6. The press fit is assured by an outside diameter of the connecting sections 6 being greater than an inside diameter of the housing 9. In this case, the adhesive bonding of the bundle 4 in the housing 9 can be dispensed with. The oversized dimension of the connecting sections 6 required for this purpose can be established based on the pressing force that is to be achieved and the material properties of the connecting section 6 and of the housing 9.

The invention claimed is:

1. A method for producing a heat exchanger for an oxygenator, comprising:
providing multiple tube sections, each having a longitudinal tube axis;
disposing the tube sections to form a bundle having a longitudinal bundle axis and opposed ends, wherein the longitudinal tube axes are oriented parallel to each other;
joining the tube sections to each other by way of at least one of chemical and physical bonded joints and thus building at least one connecting section of the bundle, wherein the joined tube sections and the at least one connecting section establish a prefabricated bundle which is dimensionally stable in itself and which is formed by adhesive bonding of the individual tube sections to each other, and
inserting the prefabricated bundle into a housing,
wherein the bundle is inserted into the housing in such a way that a connecting section that is disposed at each bundle end is disposed at least sectionally outside the housing, wherein the bundle is severed at the at least one connecting section, wherein the portions of the connecting sections protruding over the housing are severed.

2. The method according to claim 1, further comprising twisting the bundle about the longitudinal bundle axis after the tube sections have been connected.

3. The method according to claim 2, wherein twisting of the bundle about the longitudinal bundle axis disposes the longitudinal tube axes of the tubes of the bundle at an angle relative to the longitudinal bundle axis.

4. The method according to claim 1, wherein the housing into which the bundle is inserted is tubular.

5. The method according to claim 1, further comprising compressing the bundle along the longitudinal bundle axis after the tube sections have been connected to impart a curvature to the tube sections of the bundle.

6. The method according the claim 1, wherein the bundle is substantially cylindrical.

7. The method according to claim 1, wherein the tube sections are exclusively connected to each other by adhesive bonding.

8. The method according to claim 1, wherein the bundle is held in the housing by a press fit in the region of the connecting sections.

9. A method for producing a heat exchanger for an oxygenator, comprising:
providing multiple tube sections, each having a longitudinal tube axis;

disposing the tube sections to form a bundle having a longitudinal bundle axis, wherein the longitudinal tube axes are oriented parallel to each other; and joining the tube sections to each other by way of at least one of chemical and physical bonded joints and thus building at least one connecting section of the bundle, wherein the joined tube sections form an independent, prefabricated bundle that is dimensionally stable in itself before the prefabricated bundle is inserted into the housing, wherein the dimensionally stable bundle is formed by adhesive bonding of the individual tube sections to each other, and wherein a cross-sectional surface of the bundle is oriented perpendicularly to the longitudinal bundle axis is circular.

10. The method according to claim 9, wherein the dimensionally stable bundle is inserted into the housing and connected to the housing.

11. The method according to claim 10, wherein the inserted bundle is subsequently joined in the housing of the heat exchanger.

12. The method according to claim 9, wherein the tube sections are exclusively connected to each other by adhesive bonding.

13. A method for producing a heat exchanger for an oxygenator, comprising:

providing multiple tube sections, each having a longitudinal tube axis;

disposing the tube sections to form a bundle having a longitudinal bundle axis, wherein the longitudinal tube axes are oriented parallel to each other;

joining the tube sections to each other by way of at least one of chemical and physical bonded joints and thus building at least one connecting section of the bundle, wherein the joined tube sections and the at least one connecting section establish a prefabricated bundle which is dimensionally stable in itself and which is formed by adhesive bonding of the individual tube sections to each other, inserting the prefabricated bundle into a housing, adhesively bonding the at least one connecting section via an outer lateral surface to an inner side of the housing, wherein the adhesive used for connecting the at least one connecting section to the housing is the same adhesive as used for connecting the individual tube sections to each other.

\* \* \* \* \*